(12) United States Patent
Steele et al.

(10) Patent No.: US 6,582,677 B1
(45) Date of Patent: Jun. 24, 2003

(54) PROPELLANT COMPOSITIONS OF A PARTICULATE MEDICAMENT THAT ARE FREE OF SOLVENTS

(75) Inventors: Gerald Steele; Asit Somani, both of Loughborough; Joseph Geok Paan Lim, Shepshed, all of (GB)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 08/766,580

(22) Filed: Dec. 12, 1996

Related U.S. Application Data

(63) Continuation of application No. 08/355,106, filed on Dec. 13, 1994, now abandoned, which is a continuation of application No. 07/916,107, filed on Jul. 22, 1992, now abandoned.

(30) Foreign Application Priority Data

| Feb. 2, 1990 | (GB) | ............................................. 9002351 |
| Oct. 31, 1990 | (GB) | ............................................. 9023655 |
| Dec. 5, 1990 | (GB) | ............................................. 9026476 |
| Jan. 30, 1991 | (WO) | .............................. PCT/GB91/00133 |

(51) Int. Cl.[7] ................................................. A61K 9/12
(52) U.S. Cl. ........................... 424/45; 424/46; 424/489
(58) Field of Search ............................. 424/45, 46, 489

(56) References Cited

U.S. PATENT DOCUMENTS

| 3,047,640 A | * | 7/1962 | Sweeney et al. |
| 3,490,923 A | | 1/1970 | Eiseman |
| 4,174,295 A | * | 11/1979 | Bargigia et al. |
| 4,352,789 A | * | 10/1982 | Thiel |
| 4,847,091 A | * | 7/1989 | Illum |
| 4,945,119 A | * | 7/1990 | Smits et al. |
| 5,118,494 A | * | 6/1992 | Schultz et al. |
| 5,126,123 A | * | 6/1992 | Johnson |
| 5,173,298 A | * | 12/1992 | Meadows |
| 5,182,097 A | * | 1/1993 | Byron et al. |
| 5,190,029 A | * | 3/1993 | Byron et al. |
| 5,209,921 A | * | 5/1993 | Brobyn et al. |
| 5,225,183 A | * | 7/1993 | Purewal et al. |
| 5,248,493 A | * | 9/1993 | Brown |
| 5,290,539 A | * | 3/1994 | Marecki |
| 5,569,450 A | * | 10/1996 | Duan et al. |
| 6,221,339 B1 | * | 4/2001 | Akehurst et al. |

FOREIGN PATENT DOCUMENTS

| EP | 0372777 | * | 6/1990 |
| WO | PCT/GB90/00015 | | 7/1990 |
| WO | 92/00062 | | 1/1992 |

* cited by examiner

*Primary Examiner*—Raj Bawa
(74) *Attorney, Agent, or Firm*—Nixon & Vanderhye P.C.; George C. Wang

(57) ABSTRACT

Pressurized aerosol composition comprising a liquefied hydrofluorocarbon propellant of formula $C_xH_yF_z$ where x is an integer from 1 to 3, $y+z=2x+2$, and y and z are both at least 1; from 0.01 to 15% w/w of a particulate medicament dispersed in the liquefied hydrofluorocarbon propellant; and from 0.01 to 10% w/w of a fluorinated surfactant which is soluble in the liquefied hydrofluorocarbon propellant. The pressurized aerosol composition comprises no solvent, other than the liquefied hydrofluorocarbon propellant.

15 Claims, No Drawings

PROPELLANT COMPOSITIONS OF A PARTICULATE MEDICAMENT THAT ARE FREE OF SOLVENTS

This is a Rule 62 Continuation of application Ser. No. 08/355,106, filed Dec. 13, 1994, now abandoned, which is a Rule 62 Continuation of application Ser. No. 07/916,107, filed Jul. 22, 1992, now abandoned.

This invention relates to pressurised aerosol compositions, in particular compositions of inhalation medicaments.

Pressurised aerosols for the administration of medicaments, and indeed for other applications, conventionally contain one or more liquified chlorofluorocarbons (CFC's) as propellant. Such materials are suitable for use in such applications since they have the right vapor pressures (or can be mixed in the right proportions to achieve a vapor pressure in the right range) and are essentially taste- and odor-free.

In recent years there has been increasing concern about the depletion of the ozone layer in the upper atmosphere. This is believed to be due to the release into the atmosphere of CFC's and has led to a search for alternative agents for use in all applications of CFC's. To this end, aerosols for many applications are now pressurized using pressurised gases such as nitrogen or hydrocarbons. However, such propellants are generally not suitable for use in the administration of inhalation medicaments since they are toxic and/or the pressure within the canister falls each time the device is used which leads to unreproducible dosing.

The use of hydrofluorocarbons as aerosol propellants as also been suggested. European Patent Application 0 372 777, published after the earliest priority date of this application, states that the use of the hydrofluorocarbon propellant 134a and drug as a binary mixture or in combination with a conventional surfactant such as sorbitan trioleate does not provide formulations having suitable properties for use with pressurized inhalers and suggests that satisfactory formulations may be made by adding a compound having a higher polarity than propellant 134a, such as pentane or ethanol. It is stated that the addition of a compound of higher polarity than propellant 134a to propellant 134a provides a mixture in which increased amounts of surfactant may be dissolved compared to their solubility in propellant 134a alone. It is further stated that the presence of increased amounts of solubilized surfactant allows the preparation of stable, homogenous suspensions of drug particles. The use of such co-solvents is undesirable since they may have unsuitable properties, for example, they may be flammable and/or toxic.

U.S. Pat. No. 4,352,789 suggests the use of perfluorinated surfactants which are insoluble in CFC or perfluorinated propellants as a coating for finely divided medicament to be formulated in CFC or perfluorinated propellants.

Surprisingly, we have now found that mixtures of hydrofluorocarbons and fluorinated surfactants have properties which render them suitable for use as propellant systems for aerosol compositions.

Thus, according to the invention there is provided a pressurized aerosol composition comprising a liquefied hydrofluorocarbon propellant containing substantially no non-hydrofluorocarbon solvent, having dispersed therein a medicament and a fluorinated surfactant.

The compositions according to the invention are advantageous in that the solubility of the surfactant is such as to ensure good dispersion of the medicament and smooth operation of the aerosol valve. In particular, and in contrast to EP-A-0 372 777, the surfactants which characterize the present invention are sufficiently soluble in hydrofluorocarbons to enable them to be used without the presence of an additional substance as co-solvent.

The propellant mixtures of the present invention may also be advantageous in that they are substantially taste- and odor free and have suitable vapor pressures for the administration of medicaments by inhalation, yet are environmentally safe and acceptable, especially when compared with compositions including chlorofluorocarbons. In addition, they may be less irritant than corresponding compositions including conventional surfactants such as oleic acid and sorbitan trioleate.

A wide range of fluorinated surfactants may be used in the compositions of the present invention. The surfactant may be perfluorinated or otherwise.

Perfluorinated surfactants which may be used include ionic surfactants, both anionic and cationic, eg perfluorinated alcohol phosphate esters and their salts, perfluorinated sulphonamide alcohol phosphate esters and their salts, and perfluorinated alkyl sulphonamide alkylene quaternary ammonium salts. However, we prefer surfactants which are non-ionic.

Other surfactants may be used which, while not perfluorinated as such, contain at least one perfluorinated alkyl group.

We prefer surfactants which contain at least one ($CF_2$) group, more preferably from 2 to 60, eg 5 to 20 such groups.

We prefer surfactants which contain one or more ether or carboxylic ester linkages, more preferably from 2 to 60, eg 4 to 10 such linkages. We particularly prefer compounds which contain both ether and ester linkages.

We prefer surfactants which contain at least one ($CH_2$) group, more preferably from 2 to 60, eg 5 to 20 such groups. We further prefer surfactants which contain at least one ($OCH_2CH_2$) group, more preferably from 2 to 30, eg 3 to 10 such groups.

Preferred non-ionic surfactants include, for example fluorinated alcohols, esters, amides, N-oxides or sulphonamides. We particularly prefer polyfluoroalkyloxyethylenes of the general formula $C_mF_{2m+1}CH_2(OC_2H_4)_nOH$ in which m is an integer from 7 to 18 and n is an integer from 2 to 6. Other preferred surfactants include:

$(CF_3)_2CFO(CF_2)_zCONH(CH_2)_3N(O)(CH_3)_2$,
$(CF_3)_2CFOCF_2CF_2CH_2CH_2(OCH_2CH_2)_zOH$,
in which z is an integer from about 2–20,
$CF_3CF_2CF_2O(CF(CF_3)CF_2CF_2O)_nCF_2CF_2CF_3$,
in which n is an integer from about 10–60.

Further examples of preferred surfactants are the following:

The fluoroaliphatic polymeric esters known as FC 430 and FC 431, available from 3M. These are believed to be acrylic polymers having a fluorinated portion based on

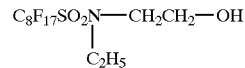

and a portion including an ethylene/propylene oxide block copolymer. These surfactants may be supplied as a 50:50 mixture with ethyl acetate, the latter compound being preferably removed before the surfactant is used in accordance with the present invention.

Other fluorinated surfactants produced by 3M that may be mentioned include FC 170c, FC 171 and FC 807. We particularly prefer surfactants which have both a fluorinated portion, especially a perfluorinated portion, and a hydrophilic portion, eg a portion based on an ethylene and/or propylene oxide.

Other fluorinated surfactants which may be mentioned are ethyl perfluorooctylsulphonamide, the linear perfluoropolyether known as Fomblin-M, perfluorodecalin and tris(1H, 1H, 5H-octafluoropentyl)phosphate. All of these are available from Fluorochem Ltd.

Mixtures of fluorinated surfactants may also be used, eg mixtures of two or more of the fluorinated surfactants listed above. Alternatively, mixtures may be used of one or more fluorinated surfactants with one or more of the surfactants conventionally used in aerosol compositions, eg CFC-pressurized compositions. Examples of such conventional surfactants are: natural oils, sorbitan oleates, eg monooleate and trioleate, sorbitan monolaurate, monoglycerides, eg glyceryl monooleate, monostearate and monolaurate, lecithins, oleic acid, etc.

Other surfactants and adjuvants that may be added include poloxamers and/or polyethylene glycols, eg PEG 1000 and PEG 1500.

In the present context, the term 'hydrofluorocarbon' is to be taken to mean a compound of general formula

in which x is an integer from 1 to 3, y+z=2x+2 and y and z are both at least 1.

Particular hydrofluorocarbons of interest are $CF_3CFH_2$ (Propellant 134a), $CH_3CHF_2$ (Propellant 152a) and $CF_3CHFCF_3$ (Propellant 227). We particularly prefer compositions including propellant 227.

In general the vapor pressure of the mixture should be in the range suitable and permitted for aerosol propellants. The, vapor pressure may be varied by mixing one or more hydrofluorocarbons and/or some other suitable vapor pressure modifying agent in appropriate proportions.

We prefer the vapor pressure of the mixture to be in the range 20 to 100 psi, more preferably 40 to 80 psi, eg about 60 psi.

The amount of surfactant in the composition will generally be from about 0.01 to 10% by weight, more preferably from about 0.1 to 5%, eg about 1%.

The medicament may be in solid, particulate form (ie the composition may be a suspension), or the active ingredient may be dissolved in the propellant.

Medicaments which may be dispersed in the propellant mixture according to the invention include any medicaments which are conventionally administered by inhalation of a pressurized aerosol formulation. Such medicaments include drugs for use in the prophylactic or remedial treatment of reversible obstructive airways disease, eg drugs such as sodium cromoglycate, nedocromil sodium, inhaled steroids, eg beclomethasone diproprionate, fluticosone and tipredane, and bronchodilators, eg salbutamol, reproterol, terbutaline, formoterol, pirbuterol, isoprenaline, salmeterol, fenoterol and salts thereof, and anticholinergic agents such as ipratropium bromide and atropine.

Where the active ingredient is solid, it preferably has a particle size distribution such that a high proportion of the particles are of a size capable of penetrating deep into the lung. In particular, the active ingredient is preferably in a form having a mass median diameter of from 0.1 to 10 μm, more preferably from 0.1 to 4 μm, eg about 2 or 3 μm.

We prefer the medicament to have a mass median diameter in the range 0.01 to 10 microns, more preferably from 1to 5 microns. The composition preferably comprises from 0.01 to 15, preferably from 0.1 to 10, and most preferably from 0.5 to 5% w/w medicament.

In producing the compositions according to the invention, a container equipped with a valve is filled with a propellant containing the finely-divided medicament. The container may first be charged with a weighed amount of medicament which has been ground to a predetermined particle size, or with a slurry of powder in the cooled liquid propellant. The container may alternatively be filled by introducing powder and propellant by the normal cold filling method, or a slurry of the powder in one component of the propellant may be placed in the container, the valve sealed in place, and the balance of the propellant then introduced by pressure filling through the valve nozzle. As a further alternative a bulk quantity of the total composition may be filled into the container through the valve.

The invention will now be illustrated, but in no way limited, by the following Example.

EXAMPLE

Compositions of the were prepared by cold filling of the ingredients into aluminium aerosol canisters which were then sealed by crimping a 5 μl or 100 μl aerosol valve in place.

The following combinations of micronised active ingredient, surfactant and propellant were used, removing solvent from the surfactant where necessary:

| | | |
|---|---|---|
| 1. | Nedocromil sodium | 0.200 g |
| | FC 431 | 0.061 g |
| | Propellant 134a | 11.979 g |
| 2. | Tipredane | 0.100 g |
| | FC 431 | 0.071 g |
| | Propellant 227 | 13.949 g |
| 3. | Sodium cromoglycate | 0.200 g |
| | FC 430 | 0.061 g |
| | Propellant 134a | 11.979 g |
| 4. | Sodium cromoglycate | 0.200 g |
| | FC 430 | 0.071 g |
| | Propellant 227 | 13.849 g |
| 5. | Nedocromil sodium | 0.200 g |
| | FC 430 | 0.061 g |
| | Propellant 134a | 11.979 g |
| 6. | Nedocromil sodium | 0.200 g |
| | FC 430 | 0.071 g |
| | Propellant 227 | 13.849 g |
| 7. | Salbutamol sulphate | 0.040 g |
| | FC 431 | 0.061 g |
| | Propellant 134a | 12.139 g |
| 8. | Fenoterol hydrobromide | 0.040 g |
| | FC 430 | 0.071 g |
| | Propellant 227 | 14.009 g |

In all cases stable suspensions of the active ingredient in the propellant were obtained.

What is claimed is:

1. A pressurized aerosol composition comprising:

a liquefied hydrofluorocarbon propellant of general formula $C_xH_yF_z$ where x is an integer from 1 to 3, y+z=2x+2, and y and z are both at least 1;

from 0.01 to 15% w/w of a particulate medicament dispersed in said liquefied hydrofluorocarbon propellant; and from 0.01 to 10% w/w of a fluorinated surfactant which is soluble in said liquefied hydrofluorocarbon propellant;

wherein the pressurized aerosol composition comprises no solvent, other than the liquefied hydrofluorocarbon propellant.

2. A composition according to claim 1, wherein said liquefied hydrofluorocarbon propellant is selected from the group consisting of $CF_3CFH_2$, $CF_3CHFCF_3$ and mixtures thereof and the fluorinated surfactant is non-ionic.

3. A composition according to claim 2, wherein the non-ionic fluorinated surfactant contains at least one ($CF_2$) group.

4. A composition according 2, wherein the non-ionic fluorinated surfactant contains one or more ether or carboxylic ester linkages.

5. A composition according to claim 2, wherein the non-ionic fluorinated surfactant contains at least one ($CH_2$) group.

6. A composition according to claim 2, wherein the medicament is selected from the group consisting of sodium cromoglycate, nedocromil sodium, beclomethasone dipropionate, fluticasone, tipredane, ipratropium bromide, atropine or a bronchodilator selected from salbutamol, reproterol, terbutaline, formoterol, pirbuterol, isoprenaline, salmeterol, fenoterol and a salt of any one thereof.

7. A composition according to claim 2, wherein the non-ionic fluorinated surfactant contains from 2 to 60 ($CF_2$) groups.

8. A composition according to claim 2, wherein the non-ionic fluorinated surfactant contains from 2 to 60 ether or carboxylic ester linkages.

9. A composition according to claim 2, wherein the non-ionic fluorinated surfactant contains both ether and carboxylic ester linkages.

10. A composition according to claim 2, wherein the non-ionic fluorinated surfactant contains 2 to 60 ($CH_2$) groups.

11. A composition according to claim 2, wherein the non-ionic fluorinated surfactant contains from 2 to 30 ($OCH_2CH_2$) groups.

12. A composition according to claim 2, wherein the non-ionic fluorinated surfactant is a polyfluoroalkyloxyethylene of the general formula $C_mF2_{m+1}CH_2(OC_2H_4)_nOH$ in which m is an integer from 7 to 18 and n is an integer from 2 to 6.

13. A composition according to claim 2, wherein the non-ionic fluorinated surfactant is selected from the group consisting of $(CF_3)_2CFO(CF_2)_zCONH(CH_2)_3N(O)CH_3)_2$ in which z is an integer from 2 to 20, $CF_3CFOCF_2CF_2CH_2CH_2(OCH_2CH_2)_zOH$ in which z is an integer from 2 to 20, $CF_3CF_2CF_2O(CF(CF_3)CF_2CF_2O)_nCF_2CF_2CF_3$ in which n is an integer from 10 to 60, and fluoroaliphatic polymeric esters having a fluorinated portion based on

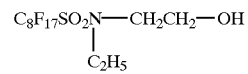

and a portion including an ethylene/propylene oxide block copolymer.

14. A composition according to claim 2, wherein the liquefied hydrofluorocarbon propellant contains $CF_3CHFCF_3$.

15. A pressurized aerosol composition comprising:
 a liquefied hydrofluorocarbon propellant of general formula $C_xH_yF_z$ where x is an integer from 1 to 3, $y+z=2x+2$, and y and z are both at least 1;
 from 0.05 to 15% w/w of a particulate medicament dispersed in said liquefied hydrofluorocarbon propellant; and
 from 0.1 to 10% w/w of a fluorinated surfactant which is soluble in said liquefied hydrofluorocarbon propellant;
 wherein the pressurized aerosol composition comprises no solvent.

* * * * *